(12) United States Patent
Lee et al.

(10) Patent No.: US 10,983,101 B2
(45) Date of Patent: Apr. 20, 2021

(54) METHYLBENZENE GAS SENSOR USING PALLADIUM-CONTAINING COBALT OXIDE NANOSTRUCTURES AND METHOD FOR MANUFACTURING THE SAME

(71) Applicant: Korea University Research and Business Foundation, Seoul (KR)

(72) Inventors: Jong-Heun Lee, Seoul (KR); Yunchan Kang, Seoul (KR); Ji-Wook Yoon, Seoul (KR); Su-Jin Hwang, Suwon-Si (KR)

(73) Assignee: Korea University Research and Business Foundation, Seoul (KR)

( * ) Notice: Subject to any disclaimer, the term of this patent is extended or adjusted under 35 U.S.C. 154(b) by 230 days.

(21) Appl. No.: 15/551,484

(22) PCT Filed: May 12, 2015

(86) PCT No.: PCT/KR2015/004765
§ 371 (c)(1),
(2) Date: Aug. 16, 2017

(87) PCT Pub. No.: WO2016/133245
PCT Pub. Date: Aug. 25, 2016

(65) Prior Publication Data
US 2018/0031532 A1  Feb. 1, 2018

(30) Foreign Application Priority Data
Feb. 16, 2015  (KR) .......................... 10-2015-0023080

(51) Int. Cl.
*G01N 27/12* (2006.01)
*G01N 33/00* (2006.01)
(Continued)

(52) U.S. Cl.
CPC ....... *G01N 33/0027* (2013.01); *G01N 27/127* (2013.01); *G01N 33/0047* (2013.01);
(Continued)

(58) Field of Classification Search
CPC ............. G01N 33/0027; G01N 27/127; G01N 33/0047; G01N 27/4074; G01N 27/4075;
(Continued)

(56) References Cited

U.S. PATENT DOCUMENTS

| | | | |
|---|---|---|---|
| 9,476,862 B2 * | 10/2016 | Motayed | G01N 33/0031 |
| 2003/0139003 A1 * | 7/2003 | Gole | G01N 27/128 |
| | | | 438/200 |
| 2016/0025695 A1 * | 1/2016 | Lee | G01N 27/127 |
| | | | 73/31.05 |

FOREIGN PATENT DOCUMENTS

| | | |
|---|---|---|
| KR | 20110006800 A | 1/2011 |
| KR | 20120045711 A | 5/2012 |
| KR | 20140125897 A | 10/2014 |

OTHER PUBLICATIONS

Park et al., Solvothermal synthesis and gas-sensing performance of Co3O4 hollow nanospheres, Sensors and Actuatros B (2009); 136:494-498.

(Continued)

*Primary Examiner* — Lisa M Caputo
*Assistant Examiner* — Alex T Devito
(74) *Attorney, Agent, or Firm* — Fox Rothschild LLP

(57) ABSTRACT

Provided is an oxide semiconductor gas sensor with improved performance that senses selectively methylbenzene gases with high sensitivity. The gas sensor includes a gas sensing layer composed of palladium (Pd)-loaded cobalt oxide (Co₃O₄) nanostructures. The response of the gas sensor according to the present invention to xylene gas at a concentration as low as 5 ppm is at least 150 times higher than that to ethanol gas. The response of the gas sensor to (Continued)

toluene gas at a concentration as low as 5 ppm is at least 100 times higher than that to ethanol gas. In addition, the oxide semiconductor gas sensor has the ability to selectively detect methylbenzene gases, including xylene and toluene (with at least 30-fold higher response to xylene and at least 15 times higher response to toluene than that to ethanol gas).

16 Claims, 10 Drawing Sheets

(51) Int. Cl.
   *H01L 21/02* (2006.01)
   *H01L 29/06* (2006.01)
   *H01L 29/24* (2006.01)

(52) U.S. Cl.
   CPC .... *H01L 21/0242* (2013.01); *H01L 21/02491* (2013.01); *H01L 21/02565* (2013.01); *H01L 21/02601* (2013.01); *H01L 21/02628* (2013.01); *H01L 29/0665* (2013.01); *H01L 29/245* (2013.01)

(58) Field of Classification Search
   CPC ........... H01L 21/0242; H01L 21/02491; H01L 21/02565; H01L 21/02601; H01L 21/02628; H01L 29/0665; H01L 29/245; B82B 1/008
   See application file for complete search history.

(56) References Cited

OTHER PUBLICATIONS

Wang et al., "Well-dispersed Palladium Supported on Ordered Mesoporous Co3O4 for Catalytic Oxidation of o-Xylene," Applied Catalysis B, Encironmental (2013): 38 pages.
European Search Report dated Oct. 5, 2018 for European Application No. 15882778.2 (7 pages).
Hong et al., "One-Pot Synthesis of Pd-Loaded SnO2 Yolk-Shell Nanostructures for Ultraselective Methyl Benzene Sensors," Chem. Eur. J. (2014); 20:2737-2741.

* cited by examiner

[Fig. 1]
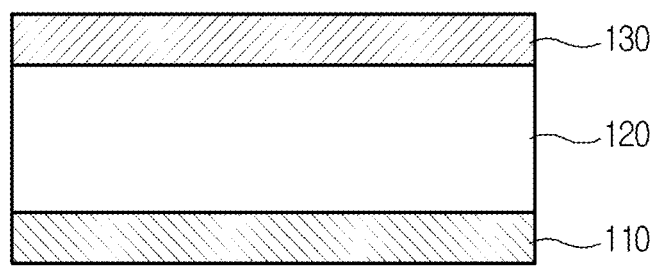
[Fig. 2]
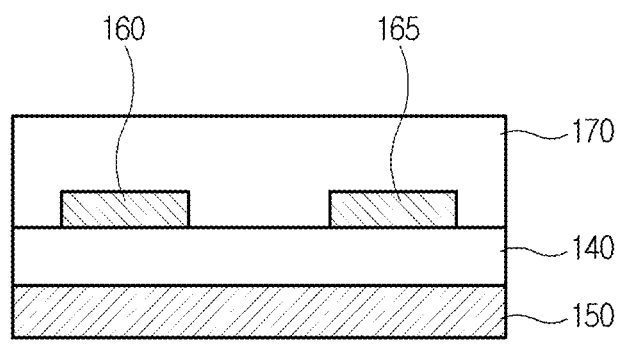

[Fig. 3]
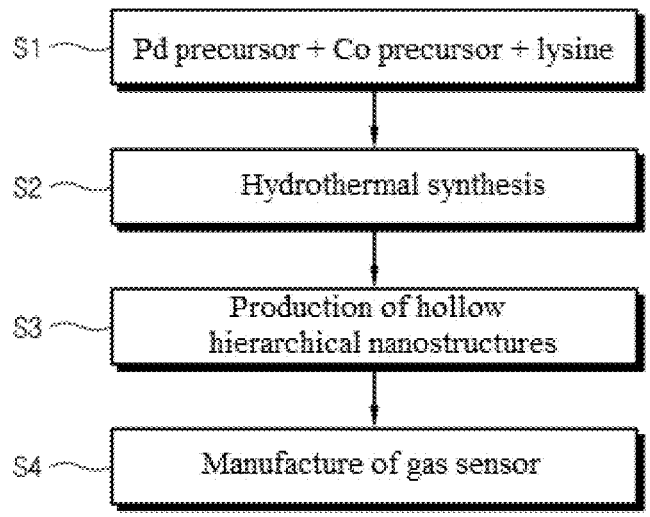
S1 — Pd precursor + Co precursor + lysine
S2 — Hydrothermal synthesis
S3 — Production of hollow hierarchical nanostructures
S4 — Manufacture of gas sensor
[Fig. 4]
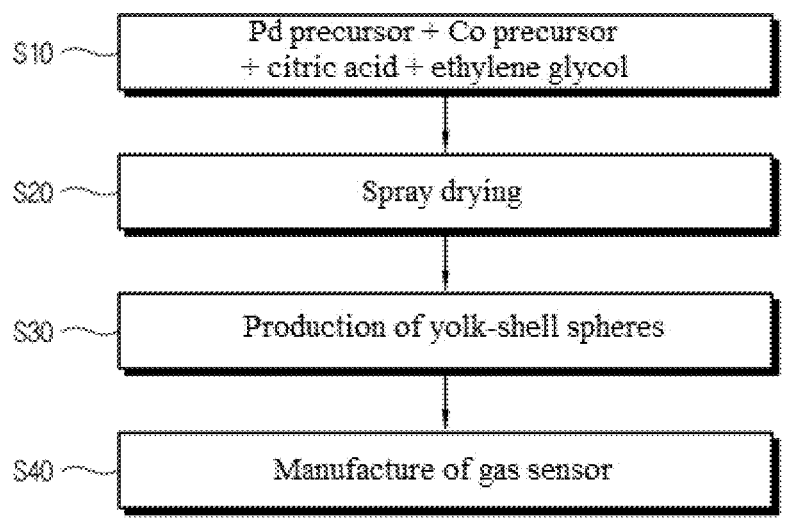
S10 — Pd precursor + Co precursor + citric acid + ethylene glycol
S20 — Spray drying
S30 — Production of yolk-shell spheres
S40 — Manufacture of gas sensor

[Fig. 5]
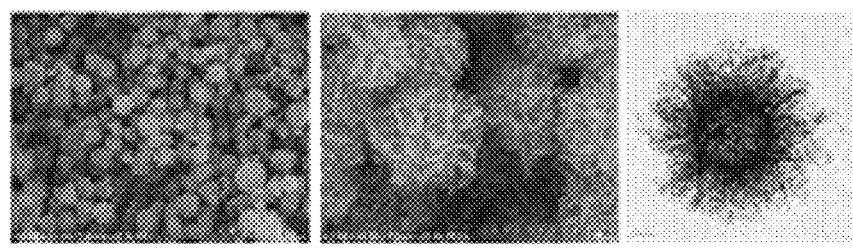
(a) Example 1
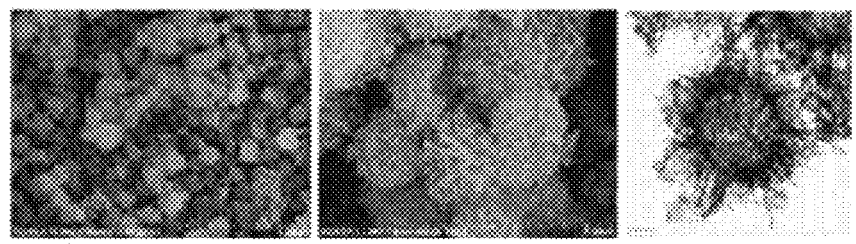
(b) Comparative Example 1-1
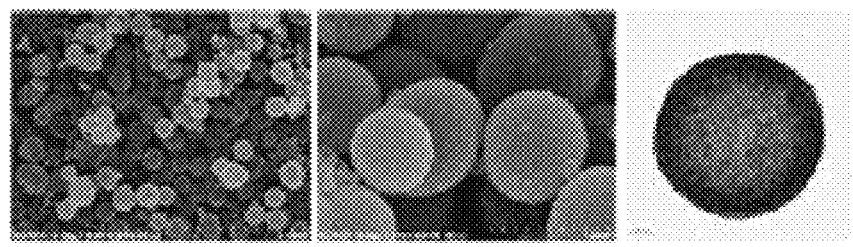
(c) Comparative Example 1-2

[Fig. 6]
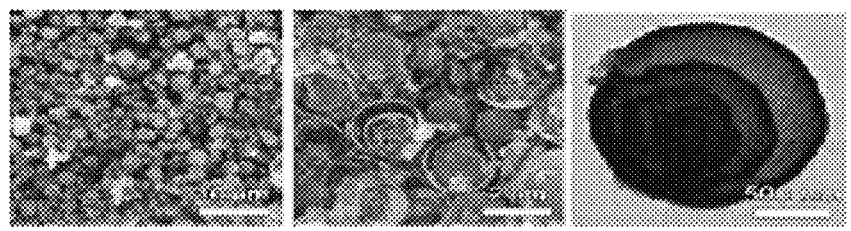
(a) Example 2
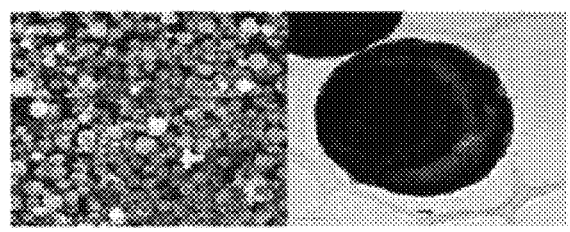
(b) Comparative Example 2-1
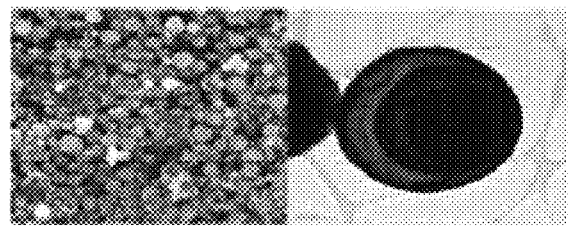
(c) Comparative Example 2-2
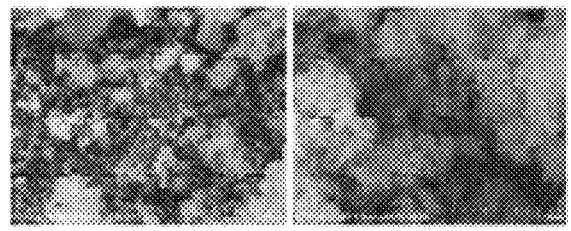
(d) Comparative Example 3

[Fig. 7]
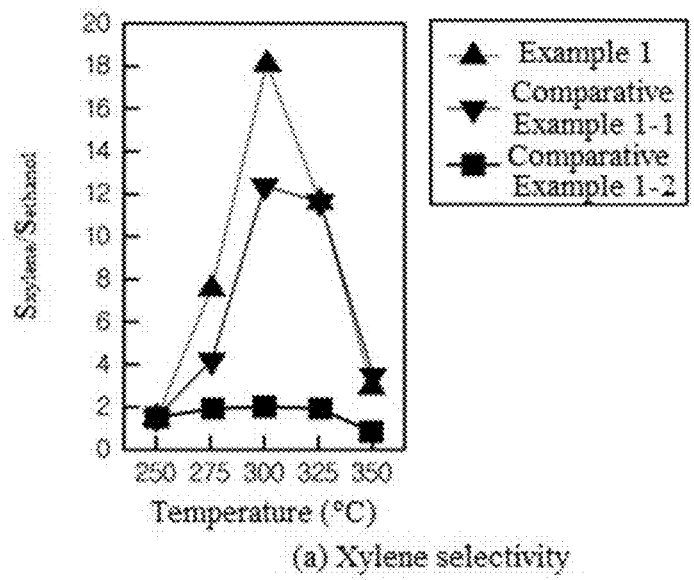
(a) Xylene selectivity
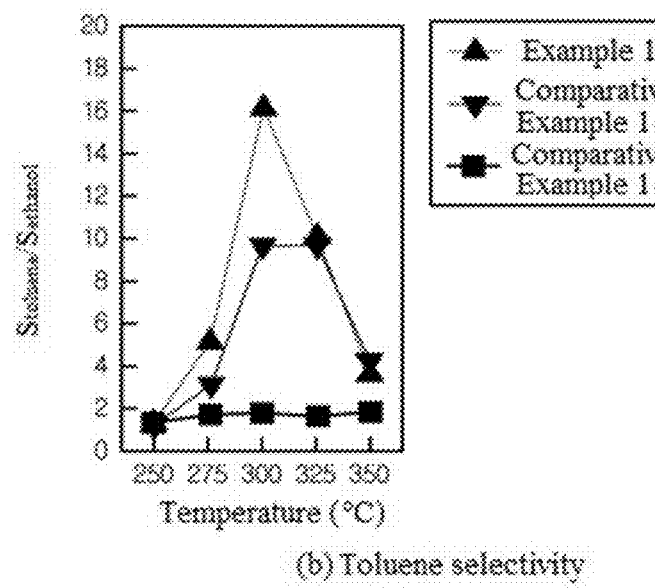
(b) Toluene selectivity

[Fig. 8]
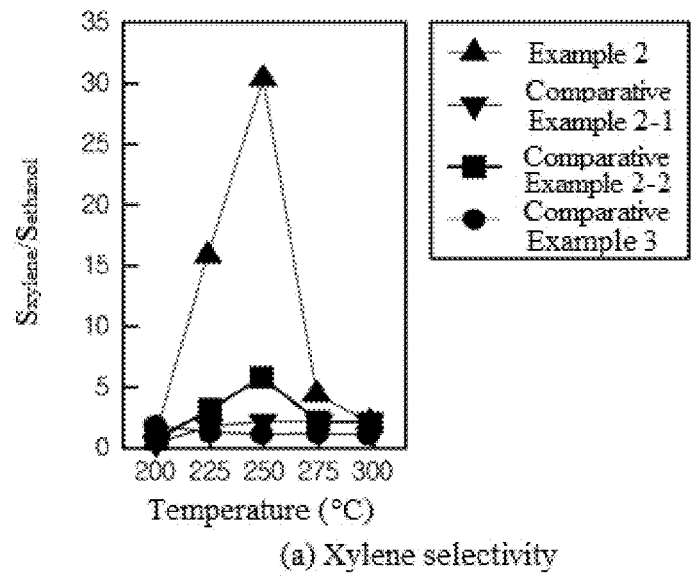
(a) Xylene selectivity
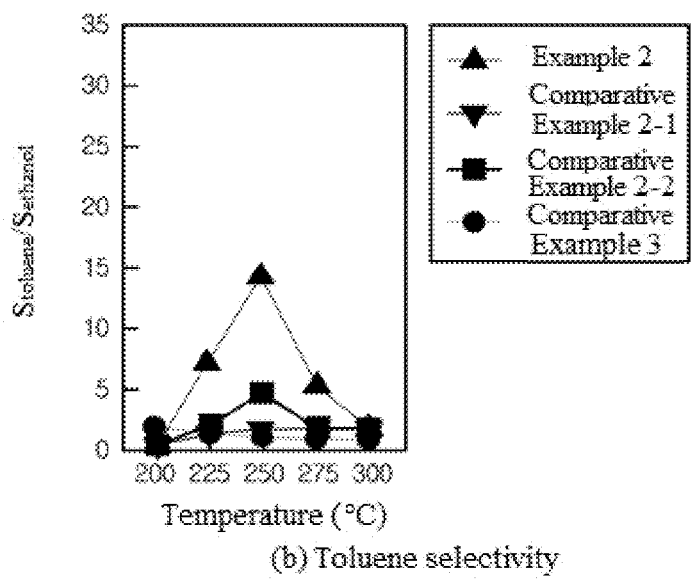
(b) Toluene selectivity

[Fig. 9]
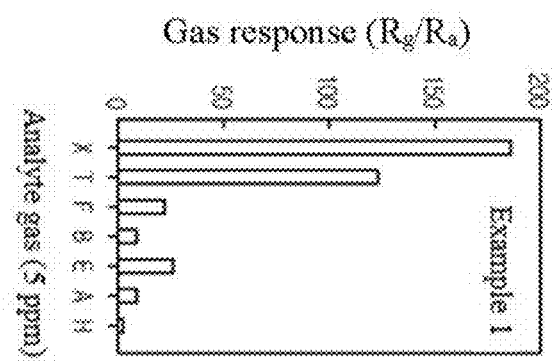
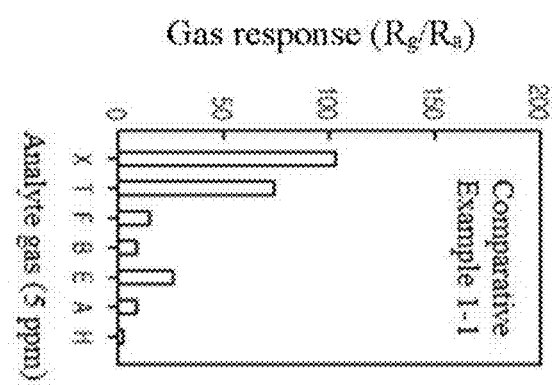
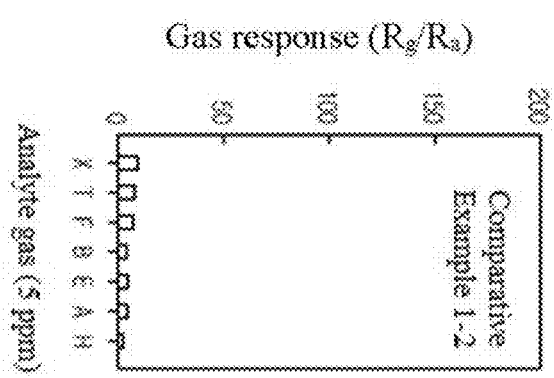

[Fig. 10]
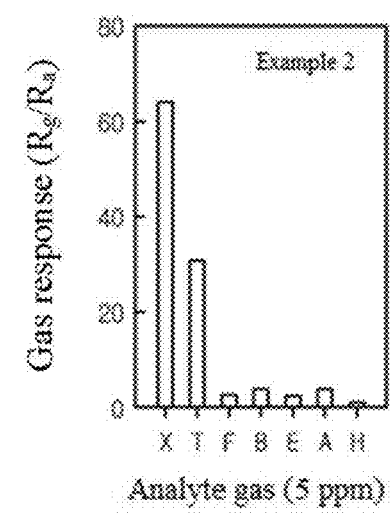
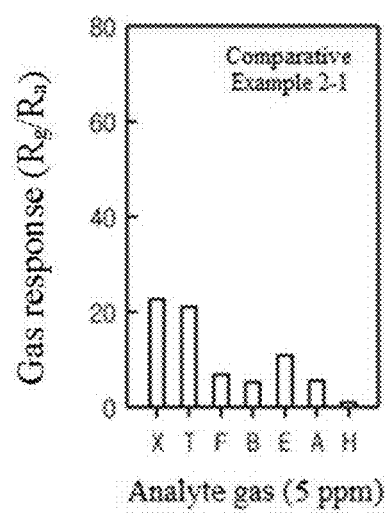
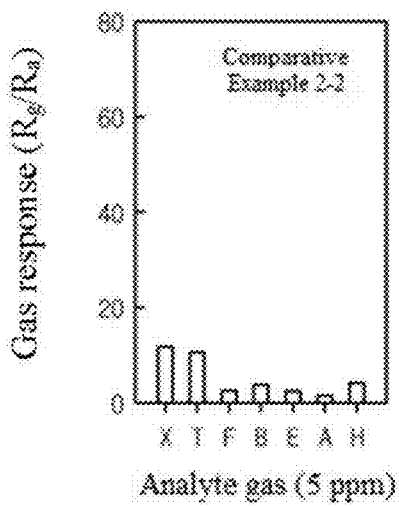
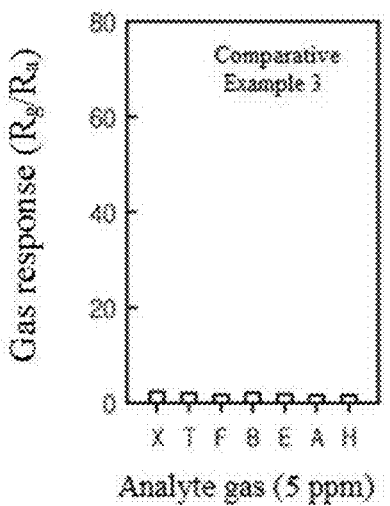

[Fig. 11]
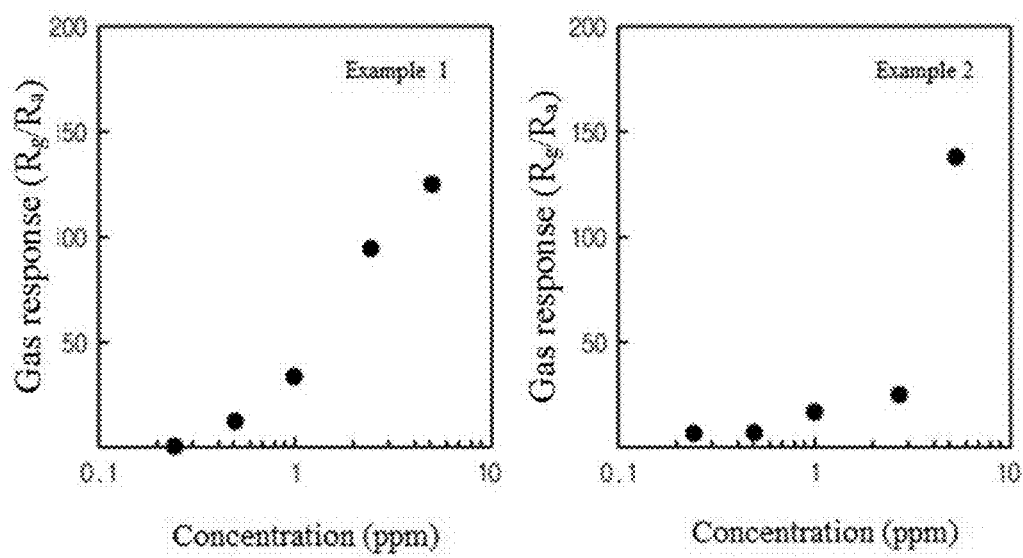

METHYLBENZENE GAS SENSOR USING PALLADIUM-CONTAINING COBALT OXIDE NANOSTRUCTURES AND METHOD FOR MANUFACTURING THE SAME

TECHNICAL FIELD

The present invention relates to an oxide semiconductor gas sensor and a method for manufacturing the same. More specifically, the present invention relates to a gas sensor having a new composition specialized for the detection of a specific target gases and a method for manufacturing the gas sensor.

BACKGROUND ART

Oxide semiconductor gas sensors can be miniaturized and integrated, are inexpensive, have high sensitivity and fast response, and have the ability to determine gas concentrations as electrical signals using simple circuits. Due to these advantages, oxide semiconductor gas sensors are widely used in various applications, such as detection of explosive gases, detection of exhaust gases from automobiles, measurement of driver's blood alcohol levels, and detection of industrial gases. With the recent advances in high-tech industries and rapidly growing interest in human health and environmental pollution, there has been an increasing demand for gas sensors for more precise detection of indoor/outdoor environmental gases, gas sensors for self-diagnosis of diseases, and gas sensors that can be used in high-performance artificial olfactory sensors mountable on mobile devices. Under such circumstances, there has also been an increasing demand for oxide semiconductor gas sensors that can detect target gases at very low concentrations with high sensitivity and high selectivity. However, most n-type oxide semiconductors (e.g., $SnO_2$, $In_2O_3$, $Fe_2O_3$, and ZnO) developed hitherto as gas sensing materials exhibit similar sensitivities to all gases, that is, poor selectivity, despite their excellent gas sensing properties. p-type oxide semiconductors (e.g., NiO, CuO, $Co_3O_4$, and $Cr_2O_3$) are still in an early stage of research and development due to their low gas sensitivity.

Volatile organic compounds known to be harmful to humans are gases that need to be detected. Since volatile organic compounds are released from various sources, such as furniture, solvents, paints, it is very important to detect the concentration of harmful volatile organic compounds in indoor/outdoor environments. Representative substances harmful to humans in indoor/outdoor environments are volatile organic compounds, such as benzene, xylene, toluene, formaldehyde, and alcohol. Particularly, benzene, xylene, and toluene are aromatic hydrocarbons that are similar in molecular structure but have different influences on humans. Benzene is known as a carcinogenic substance to cause cancers, such as leukemia, whereas xylene and toluene were reported to cause various respiratory and nervous diseases, such as ocular diseases and migraine.

Most oxide semiconductor gas sensors show similar sensitivities to the above five volatile organic compounds. However, these volatile organic compounds need to be individually sensed with high selectivity because their influences on humans are very different, as described above. In the case where the total amount rather than the individual amounts of aromatic hydrocarbons is simply sensed, it is impossible to properly determine how to respond to and solve individual sources of pollution. Alcohol gas is frequently produced and formaldehyde is also found at a significantly high concentration during indoor activities, such as cooking and drinking. For these reasons, gas sensors for detecting indoor environmental pollutants should have low sensitivities to alcohol and formaldehyde. However, most oxide semiconductor gas sensors developed hitherto are highly sensitive to alcohol.

Methylbenzene gases, including xylene and toluene, are volatile organic compounds that have similar influences on humans. Methylbenzene gases are fatal indoor environmental gases that negatively affect respiratory and brain activities upon long-term inhalation. Thus, it is very important and necessary to develop oxide semiconductors capable of detecting methylbenzenes with high sensitivity and high selectivity.

SUMMARY

One object of the present invention is to provide an oxide semiconductor gas sensor with improved performance that senses selectively methylbenzene gases with high sensitivity.

A further object of the present invention is to provide a method for manufacturing the oxide semiconductor gas sensor.

One aspect of the present invention provides a gas sensor for detecting methylbenzene gases including a gas sensing layer composed of palladium (Pd)-loaded cobalt oxide ($Co_3O_4$) nanostructures.

The nanostructures may be hollow hierarchical nanostructures or yolk-shell spheres. The palladium is preferably loaded in an amount larger than 0 at % and not larger than 1.7 at %.

A further aspect of the present invention provides a method for manufacturing the gas sensor, including forming palladium-loaded cobalt oxide nanostructures and forming a gas sensing layer using the nanostructures.

The step of forming palladium-loaded cobalt oxide nanostructures may include: mixing a cobalt precursor with a palladium precursor in a mixed solvent of anhydrous ethanol and deionized water to prepare a raw material solution; subjecting the raw material solution to hydrothermal synthesis by heating; and washing the reaction solution by centrifugation and drying the precipitate.

In an alternative embodiment, the step of forming palladium-loaded cobalt oxide yolk-shell nanostructures may include: mixing a cobalt precursor, citric acid, and a palladium precursor to prepare a spray solution; and spraying, drying, and heat treatment of spheric precursors.

The gas sensor of the present invention uses surface-modified nanostructures, such as palladium-loaded cobalt oxide hollow hierarchical nanostructures or yolk-shell spheres. The gas sensor of the present invention can detect methylbenzene gases, such as xylene and toluene, which are harmful environmental gases that have similar influences on humans, with high sensitivity and high selectivity.

The hollow hierarchical nanostructures or the yolk-shell spheres are structures advantageous for gas diffusion and reaction. The palladium loading increases the reaction of cobalt oxide with methylbenzene gases as specific target gases due to the catalytic activity of palladium and cobalt oxide also plays the role of an oxidation catalyst to promote the methylbenzene sensing, achieving ultrahigh sensitivity and high selectivity of the gas sensor to methylbenzene gases. Particularly, the gas sensor of the present invention has very low cross-sensitivity to benzene gas, enabling selective detection of methylbenzene gases as harmful environmental gases. Therefore, the gas sensor of the present invention can advantageously provide an appropriate solution to harmful environmental gases.

In addition, the gas sensor of the present invention does show negligible response to alcohol gas occurring during indoor activities, such as cooking and drinking, due to its low alcohol sensitivity and is thus advantageous in selectively sensing xylene and toluene. Furthermore, the gas sensor of the present invention is very advantageous in selectively sensing xylene and toluene because of its very low cross-responses to formaldehyde, which is usually detected at a high concentration indoors.

The gas sensor of the present invention uses palladium-loaded cobalt oxide nanostructures as raw materials that can be easily synthesized at one time on a large scale. According to the method of the present invention, the same sensing properties of the gas sensor can be obtained irrespective of how to add palladium and the structure of the cobalt oxide. Based on this, the methylbenzene gas sensor can bring better results in terms of selectivity over conventional gas sensors.

According to the present invention, the use of the palladium-loaded cobalt oxide nanostructures allows the p-type oxide semiconductor gas sensor to have greatly increased sensitivity and superior stability against external humidity.

BRIEF DESCRIPTION OF THE DRAWINGS

FIGS. 1 and 2 are schematic cross-sectional views illustrating exemplary structures of a gas sensor according to the present invention.

FIG. 3 is a flowchart illustrating a method for manufacturing a gas sensor according to one embodiment of the present invention.

FIG. 4 is a flowchart illustrating a method for manufacturing a gas sensor according to an alternative embodiment of the present invention.

FIG. 5 shows SEM and TEM images of powders produced in Example 1 and Comparative Examples 1-1 and 1-2.

FIG. 6 shows SEM and TEM images of powders produced in Example 2 and Comparative Examples 2-1, 2-2, and 3.

FIG. 7 shows the influences of Pd loading on the selectivities of gas sensors manufactured using $Co_3O_4$ hollow hierarchical nanostructures.

FIG. 8 shows the selectivities of gas sensors manufactured using $Co_3O_4$ yolk-shell spheres loaded with Pd at various concentrations to methylbenzenes over ethanol.

FIG. 9 shows the responses of gas sensors manufactured in Example 1 and Comparative Examples 1-1 and 1-2 to various gases at 275° C.

FIG. 10 shows the responses of gas sensors manufactured in Example 2 and Comparative Examples 2-1, 2-2, and 3 to various gases at 250° C.

FIG. 11 shows the responses of gas sensors manufactured in Examples 1 and 2 to xylene gas at varying concentrations (0.25-5.0 ppm).

DETAILED DESCRIPTION

Figure 12A:
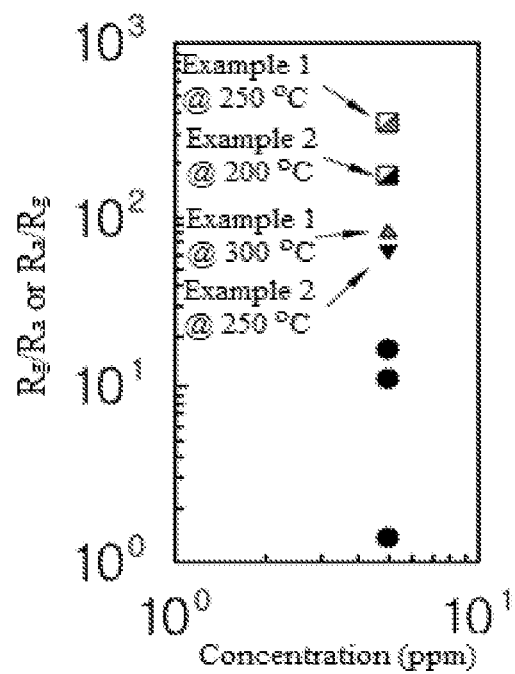
FIGS. 12a, 12b, 12c and 12d compare the responses of gas sensors manufactured in Examples 1 and 2 to methylbenzenes and the selectivities of the gas sensors to methylbenzenes over ethanol with those of conventional gas sensors reported in the literature: (12a) comparison with literature values (Sxylene); (12b) comparison with literature values (Sxylene/Sethanol); (12c) comparison with literature values (Stoluene); and (12d) comparison with literature values (Stoluene/Sethanol).

Preferred embodiments of the present invention will be now described in detail. However, the embodiments may be changed into several other forms, and the scope of the present invention should not be construed as being limited to the following embodiments. The embodiments of the present invention are intended to more comprehensively explain the present invention to those skilled in the art. Accordingly, the shapes of elements or the like shown in figures are exaggerated to emphasize distinct explanation.

A gas sensor of the present invention includes a gas sensing layer composed of palladium-loaded cobalt oxide. Prior to the present invention, high selectivity of palladium-loaded cobalt oxide only to methylbenzene gases has never been known in the art. To the best of our knowledge, this is the first report on the use and effect of palladium-loaded cobalt oxide.

FIGS. 1 and 2 are schematic cross-sectional views illustrating exemplary structures of the gas sensor according to the present invention. Each of the structures includes a gas sensing layer composed of palladium-loaded cobalt oxide. The gas sensor of the present invention is not limited to the structures illustrated in the figures and may have any structure that includes a gas sensing layer composed of palladium-loaded cobalt oxide.

In the gas sensor structure illustrated in FIG. 1, electrodes 110 and 130 are disposed on the lower and upper surfaces of a gas sensing layer 120. In the gas sensor structure illustrated in FIG. 2, a microheater 150 is disposed on the lower surface of a substrate 140, two electrodes 160 and 165 are disposed on the upper surface of the substrate 140, and a gas sensing layer 170 is formed thereon. The gas sensing layers 120 and 170 are composed of palladium-loaded cobalt oxide. If needed, the amount of palladium in each gas sensing layer may be varied.

Taking advantage of a combination of the inherent oxidative catalytic activity of palladium and the oxidative catalytic activity of cobalt oxide as a sensing material for reducing gases, the gas sensor of the present invention enables selective sensing of methyl group-containing hydrocarbon gases, that is to say, methylbenzene gases, for example, xylene and toluene. The amount of palladium loaded is preferably larger than 0 at % and not larger than 1.7 at % with respect to the amount of cobalt oxide, as confirmed by the results of experiments conducted in the Examples section that follow. If palladium is loaded in an amount exceeding 1.7 at %, the response of the gas sensor to methylbenzene gases may deteriorate.

The gas sensor including the gas sensing layer 120 or 170 composed of palladium-loaded cobalt oxide is a p-type oxide semiconductor gas sensor. When negatively charged oxygen is adsorbed to the surface of the p-type oxide semiconductor, holes around the surface gather to form a hole accumulation layer. When the p-type oxide semiconductor is exposed to a reducing gas, the reducing gas reacts with the negatively charged oxygen to inject electrons into the hole accumulation layer. As a result of recombination of the electrons and holes, the concentration of holes in the hole accumulation layer is reduced, resulting in an increase in the resistance of the sensor. Meanwhile, when the p-type oxide semiconductor is exposed to an oxidizing gas, the concentration of holes in accumulation layer increases, resulting in a reduction in the resistance of the sensor. Based on the gas sensing mechanism that a change in conductivity is caused by the surface adsorption of gas, the gas sensor of the present invention is operated.

Gas sensors using n-type oxide semiconductors ($SnO_2$, $In_2O_3$, $Cr_2O_3$, and ZnO) reported to date simultaneously show similar responses to a variety of gases, indicating their poor gas selectivity. Moreover, the gas sensors sensitively respond to humidity in air due to their air resistance as high as several to several tens of MΩ. When the gas sensors react with humidity, the air resistance of the gas sensors varies drastically, deteriorating the stability of the gas sensors. In contrast, gas sensors using p-type oxide semiconductors having an air resistance as low as a few to a few tens of KΩ undergo minimal change in resistance in air during long-term operation, indicating their long-term stability. However, p-type oxide semiconductors often suffer from difficulty in detecting gases at low concentrations because they have relatively low gas sensitivity compared to n-type oxide semiconductors. The gas sensor of the present invention can be used to develop gas sensor devices with high sensitivity and reliability because it uses a p-type oxide semiconductor that undergoes minimal change in resistance and is highly sensitive.

In the present invention, palladium is loaded in cobalt oxide as a sensing material whose structure may be varied. This palladium loading allows the gas sensor to have higher stability than n-type oxide semiconductor gas sensors and increases the sensitivity of the gas sensor to methylbenzene gases by several times compared to that of conventional gas sensors irrespective of the structure of the cobalt oxide. High selectivity of the gas sensor for methylbenzene gases can be obtained. According to the present invention, palladium is loaded in p-type oxide semiconductor cobalt oxide whose structure may be varied. This palladium loading is to take advantage of a combination of the inherent oxidative catalytic activity of palladium and the oxidative catalytic activity of cobalt oxide as a sensing material for reducing gases, bringing about a remarkable improvement in the sensitivity and selectivity of the cobalt oxide semiconductor gas sensor to methylbenzene gases. The p-type oxide semiconductor gas sensor has the advantages of superior long-term stability and high selectivity. These advantages are expected to contribute to the commercialization of the gas sensor.

As can be seen from the Examples section that follows, the palladium-loaded cobalt oxide hollow hierarchical nanostructures constituting the gas sensing layers 120 and 170 may be produced by a one-step process through hydrothermal synthesis. The hollow hierarchical nanostructures refer to structures in which plate-like primary particles aggregate to form spherical particles. The hollow hierarchical structures have a large surface area, which is advantageous for gas diffusion. The palladium-loaded cobalt oxide yolk-shell spheres constituting the gas sensing layers 120 and 170 may be produced by spray drying and subsequent heat treatment. The yolk-shell spheres are also advantageous for gas diffusion. In the present invention, $Co_3O_4$, a substance to promote the oxidation of high molecular weight hydrocarbon gases with low reactivity, is produced into hollow hierarchical nanostructures or yolk-shell spheres through which the target gases enter/exit and diffuse, enabling the detection of hydrocarbon gases with high sensitivity. $Co_3O_4$ is an oxidation catalyst that serves to relatively increase the sensitivity to methylbenzenes. In addition, the inherent oxidative catalytic activity of palladium allows the gas sensor to selectively sense methyl group-containing hydrocarbon gases (xylene and toluene).

The gas sensor is manufactured by a method including forming palladium-loaded cobalt oxide nanostructures and forming a gas sensing layer 120 or 170 using the nanostructures. The nanostructures may be hollow hierarchical nanostructures or yolk-shell spheres. Hereinafter, the method will be explained based on the synthesis of the nanostructures and the fabrication of the gas sensor using the nanostructures.

FIG. 3 is a flowchart illustrating a method for manufacturing a gas sensor according to one embodiment of the present invention.

Referring to FIG. 3, a raw material solution including a palladium precursor and a cobalt precursor is prepared (step S1). Lysine may be further added to the raw material solution. Specifically, first, a cobalt precursor and lysine are added to a mixed solvent of anhydrous ethanol and deionized water. The mixture is stirred. To the resulting solution is added a palladium precursor. The mixture is stirred to prepare a raw material solution. The reason for the lysine addition is because self-assembly between the positively charged amine groups and the negatively charged carboxyl group of lysine leads to the formation of nanostructures that facilitate gas diffusion and have a large specific surface area, thus being advantageous in sensing gases.

Next, the raw material solution is subjected to hydrothermal synthesis reaction by heating (step S2). For example, the heating is performed at 180° C. for 12 hours.

The reaction solution is washed by centrifugation and dried to prepare a powder of hollow hierarchical nanostructures (step S3). If needed, the powder is annealed, for example, at 400 to 500° C. for 1 to 2 hours. This annealing is optional and does not need to perform but would be desirable because it is effective in removing residual organic materials and imparting strength to the powder.

Next, a gas sensing layer is formed using the powder of cobalt oxide hollow hierarchical nanostructures, completing the manufacture of the gas sensor illustrated in FIG. 1 or 2 (step S4). The gas sensor can be manufactured by the following procedure.

First, the powder of palladium-loaded cobalt oxide hollow hierarchical nanostructures prepared in step S3 is dispersed in an appropriate solvent or binder. The dispersion is applied to a proper substrate, for example, the substrate 140 illustrated in FIG. 2 (under which the microheater 150 is disposed and on which the two electrodes 160 and 165 are disposed). Herein, the term "application" is intended to include various techniques, such as printing, brushing, blade coating, dispensing, and micropipette dropping. Next, the solvent is removed to form a gas sensing layer. If needed, heating, i.e. annealing, may be performed to assist in removing the solvent.

FIG. 4 is a flowchart illustrating a method for manufacturing a gas sensor according to an alternative embodiment of the present invention.

Referring to FIG. 4, a spray solution including a palladium precursor, a cobalt precursor, and citric acid is prepared (step S10). Ethylene glycol may be further added to the spray solution.

Next, the spray solution is sprayed and dried (step S20).

In this step, the spray solution is sprayed to produce microdroplets. The microdroplets are placed in a reactor, and then a powder is synthesized in and recovered from the reactor. The size of the microdroplets may be controlled by various factors, such as the internal pressure of the sprayer and the concentration and viscosity of the spray solution. The reactor is heated to volatilize substantially all of the solvent from the microdroplets, leaving polymer precursors, oxides, and metal catalyst precursor components.

The powder is obtained from each of the microdroplets, and as a result, it has a size at the sub-micron to micron level without the need for additional milling and dispensing.

After step S20, the powder is annealed at 350° C. for 3 h. During annealing, the carbon precursor is decomposed stepwise from the surface to synthesize $Co_3O_4$ yolk-shell spheres (step S30).

Next, a gas sensing layer is formed using the powder of $Co_3O_4$ yolk-shell spheres, completing the manufacture of the gas sensor illustrated in FIG. 1 or 2 (step S40). The procedure for manufacturing the gas sensor is the same as that explained in step S4.

In the following Examples section, a fine powder of 0.86 wt % Pd-loaded $Co_3O_4$ hollow hierarchical nanostructures was prepared and a gas sensor was manufactured using the fine powder (Example 1). The response and selectivity of the gas sensor manufactured in Example 1 to xylene and toluene were compared with those of a gas sensor manufactured using a fine powder of pure $Co_3O_4$ hollow hierarchical nanostructures (Comparative Example 1-1) and a gas sensor manufactured using a fine powder of $Co_3O_4$ hollow hierarchical nanostructures (Comparative Example 1-2). In addition, a fine powder of 0.17 at % Pd-loaded $Co_3O_4$ yolk-shell spheres was prepared and a gas sensor was manufactured using the fine powder (Example 2). The sensitivity and selectivity of the gas sensor manufactured in Example 2 to xylene and toluene were compared with those of a gas sensor manufactured using a fine powder of pure $Co_3O_4$ yolk-shell spheres (Comparative Example 2-1), a gas sensor manufactured using a fine powder of 1.7 at % Pd-loaded $Co_3O_4$ yolk-shell spheres (Comparative Example 2-2), and a gas sensor manufactured using a commercial $Co_3O_4$ powder (Comparative Example 3).

EXAMPLES

Example 1

0.010 M cobalt (II) acetate ($C_4H_6CoO_4$, 99.995% trace metals basis, Sigma-Aldrich Co.) and 0.020 M L(+)-lysine ($C_6H_{14}N_2O_2$, 98%, Sigma-Aldrich Co.) were added to a mixed solvent of 47.5 ml of anhydrous ethanol and 2.5 ml of deionized water. The mixture was stirred for 5 min, followed by ultrasonic dispersion. To the resulting solution was added palladium (II) chloride ($PdCl_2$, 99.999%, Sigma-Aldrich Co.). The amount of the palladium precursor was determined such that the ratio of Pd/Co was 0.86 at %. After stirring for 10 min, the solution was subjected to hydrothermal synthesis at 180° C. for 12 h.

After completion of the reaction, the reaction solution was washed five times by centrifugation and dried for 24 h to yield a precursor. The resulting fine powder of hollow hierarchical nanostructures was annealed at 400° C. for 1 h to obtain palladium-loaded cobalt oxide hollow hierarchical nanostructures. The annealed fine powder was mixed with deionized water, dropped onto an alumina substrate on which an Au electrode had been formed, and annealed at 400° C. for 24 h, completing the manufacture of the gas sensor illustrated in FIG. 1. The sensor was placed in a quartz tube electric furnace (inner diameter 30 mm) whose temperature was controlled to 250-350° C. and pure air and air+mixed gas were alternately fed into the furnace. During the feeding, changes the in resistance of the sensor were measured. The gases were previously mixed and their concentrations were rapidly varied using a 4-way valve. The total flow rate was fixed at 500 SCCM so that there was no temperature difference when the gas concentrations were varied.

Example 2

Palladium nitrate ($Pd(NO_3)_2$, Sigma-Aldrich Co.) was added to a solution of 0.15 M cobalt nitrate hexahydrate ($Co(NO_3)_2 \cdot 6H_2O$, Junsei. Co.), 0.10 M citric acid ($C_6H_8O_7 \cdot H_2O$, Samchun. Co.), and ethylene glycol ($C_2H_6O_2$, Samchun. Co.) in deionized water. The amount of the palladium precursor was determined such that the ratio of Pd/Co was 0.17 at %. A two-fluid nozzle was used to spray the solution into a spray drier whose inlet and outlet temperatures were adjusted to 130° C. and 300° C., respectively. The pressure was fixed to 2.4 bar. After completion of the reaction, the resulting precursor was annealed to 350° C. at a rate of 10° C./min for 3 h to obtain Pd-loaded $Co_3O_4$ yolk-shell spheres. Thereafter, a sensor was manufactured using the Pd-loaded $Co_3O_4$ yolk-shell spheres and the gas sensing properties of the sensor were measured in the same manner as in Example 1.

Comparative Example 1-1

A gas sensor was manufactured and the gas sensing properties of the sensor were measured in the same manner as in Example 1, except that the use of palladium (II) chloride was omitted to obtain a fine powder of pure cobalt oxide hollow hierarchical nanostructures.

Comparative Example 1-2

0.010 M cobalt (II) acetate ($C_4H_6CoO_4$, 99.995% trace metals basis, Sigma-Aldrich Co.) and 0.040 M L(+)-lysine ($C_6H_{14}N_2O_2$, 98%, Sigma-Aldrich Co.) were added to 50 ml of anhydrous ethanol. The mixture was stirred for 5 min, dispersed by sonication, and subjected to hydrothermal synthesis at 180° C. for 12 h. After completion of the reaction, the reaction solution was washed 5 times by centrifugation and dried for 24 h to yield a precursor. The resulting fine powder of hollow hierarchical nanostructures was annealed at 400° C. for 1 h to obtain cobalt oxide hollow hierarchical nanostructures. Thereafter, a sensor was manufactured using the cobalt oxide hollow hierarchical nanostructures and the gas sensing properties of the sensor were measured in the same manner as in Example 1.

Comparative Example 2-1

A fine powder of pure cobalt oxide yolk-shell spheres was produced in the same manner as in Example 2, except that the use of palladium nitrate was omitted. Thereafter, a gas sensor was manufactured using the fine powder of pure cobalt oxide yolk-shell spheres and the gas sensing properties of the sensor were measured in the same manner as in Example 1.

Comparative Example 2-2

1.7 at % Pd-loaded $Co_3O_4$ yolk-shell spheres were obtained in the same manner as in Example 2, except that the ratio of Pd/Co was changed to 1.7 at %. Thereafter, a gas sensor was manufactured using the Pd-loaded $Co_3O_4$ yolk-shell spheres and the gas sensing properties of the sensor were measured in the same manner as in Example 1.

Comparative Example 3

A commercial cobalt oxide ($Co_3O_4$, 99.5% trace metal basis, Sigma-Aldrich) was annealed at 400° C. for 1 h. Thereafter, a gas sensor was manufactured using the annealed cobalt oxide and the gas sensing properties of the sensor were measured in the same manner as in Example 1.

The characteristics of the sensors manufactured in Examples 1-2 and Comparative Examples 1-1, 1-2, 2-1, 2-2, and 3 were measured at different temperatures. As a result, the sensors exhibited p-type semiconductor characteristics because their resistances were increased in all reducing gases. The gas response (S) of each sensor was defined as $R_g/R_a$ ($R_g$: resistance of the device in the corresponding gas, $R_a$: resistance of the device in air). The selectivity of the sensor for a target gas was determined from differences in the responses of the sensor to the target gas and the other gases.

When the resistance of each sensor in air was kept constant, the atmosphere was suddenly changed to xylene, toluene, benzene, formaldehyde or ethanol (5 ppm) as a target gas. Thereafter, when the resistance of the sensor in the target gas was kept constant, the atmosphere was changed to air. At this time, a change in the resistance of the sensor was measured.

FIGS. 5 and 6 show SEM and TEM images of the powders produced in Examples 1-2 and Comparative Examples 1-1, 1-2, 2-1, 2-2, and 3.

(a), (b), and (c) of FIG. 5 show the powder produced through hydrothermal synthesis in Example 1, the powder produced in Comparative Example 1-1, and the powder produced in Comparative Example 1-2, respectively. (a), (b), and (c) of FIG. 6 show the powders produced through spray drying in Example 2, the powder produced in Comparative Example 2-1, and the powder produced in Comparative Example 2-2. (d) of FIG. 6 shows the commercial powder used in Comparative Example 3.

In the powder of spherical hollow hierarchical structures produced in Example 1 ((a) of FIG. 5), plate-like primary particles assembled to form spherical particles. In the powder of yolk-shell spheres produced in Example 2 ((a) of FIG. 6), four hollow structures were further present.

Referring to (b) of FIG. 5, the powder of Comparative Example 1-1 was composed of pure $Co_3O_4$ without Pd loading and had the same structure and size as the powder of Example 1. Referring to (c) of FIG. 6, the powder of Comparative Example 1-2 had a hollow structure whose shell was relatively thick.

Referring to (b) and (c) of FIG. 6, the powders of Comparative Examples 2-1 and 2-2 had the same structure and size as the powder of Example 2 irrespective of the loading amount of Pd. Referring to (d) of FIG. 6, the powder of Comparative Example 3 was in the form of a nanopowder.

As shown in (a) of FIG. 5 and (a) of FIG. 6, the powders produced in Examples 1 and 2 had hollow hierarchical nanostructures and yolk-shell spheres with large specific surface areas and a number of pores, respectively. In the gas sensors manufactured using the hollow hierarchical nanostructures and the yolk-shell spheres, gases diffuse rapidly into the gas sensing materials. Therefore, the hollow hierarchical nanostructures and the yolk-shell spheres are optimized structures in which gases can participate in sensing reactions with the gas sensing materials.

(a) and (b) of FIG. 7 show the influences of Pd loading on the selectivities of the gas sensors manufactured using Pd-loaded $Co_3O_4$ hollow hierarchical nanostructures to xylene ($S_{xylene}/S_{ethanol}$, ratio of gas responses for xylene and ethanol) and toluene ($S_{toluene}/S_{ethanol}$, ratio of gas responses for xylene and ethanol), respectively.

The Pd-loaded $Co_3O_4$ hollow hierarchical nanostructures (Example 1) showed very high selectivities to xylene and toluene gases over ethanol gas ($S_{xylene}/S_{ethanol}$=18.1 and $S_{toluene}/S_{ethanol}$=16.1). The xylene and toluene selectivities of the powder of Comparative Example 1-1 were much lower than those of the Pd-loaded powder of Example 1 ($S_{xylene}/S_{ethanol}$=12.4 and $S_{toluene}/S_{ethanol}$=9.58). These results are believed to be because the inherent oxidative catalytic activity of the p-type oxide semiconductor $Co_3O_4$ was promoted by the hollow hierarchical nanostructures advantageous for gas diffusion, and as a result, its response to chemically stable methylbenzenes increased. The Pd loading remarkably increased the selectivities to methylbenzenes (xylene and toluene) over ethanol, indicating that Pd is a very important catalyst having the function of selectively detecting methylbenzenes. The sensor of Comparative Example 1-2 showed very similar responses to 5 ppm xylene and ethanol gases. That is, the sensor suffered from difficulty in selectively detecting methylbenzenes. This tendency shows that both structure and composition of material are important for selective detection of methylbenzenes.

FIGS. 8(a) and 8(b) show the selectivities of the gas sensors manufactured using $Co_3O_4$ yolk-shell spheres loaded with Pd at various concentrations to xylene ($S_{xylene}/S_{ethanol}$) and toluene ($S_{toluene}/S_{ethanol}$), respectively. The 0.17 at % Pd-loaded $Co_3O_4$ yolk-shell spheres (Example 2) showed very high selectivities ($S_{xylene}/S_{ethanol}$=30.1 and $S_{toluene}/S_{ethanol}$=14.5), like the 0.86 at % Pd-loaded $Co_3O_4$ hollow hierarchical nanostructures (Example 1). These results are believed to be due to the structural characteristics of the yolk-shell spheres having a number of shells and synergistic catalytic effects of Pd and cobalt oxide. The increased retention of methylbenzenes in the yolk-shell spheres maximizes the catalytic activity of Pd on methylbenzenes. In contrast, the pure $Co_3O_4$ yolk-shell spheres (Comparative Example 2-1) showed lower selectivities ($S_{xylene}/S_{ethanol}$=2.15 and $S_{toluene}/S_{ethanol}$=2.01) than the Pd-loaded $Co_3O_4$ hollow hierarchical nanostructures of Example 1 despite their same structure. These results again demonstrate that Pd is a very important catalyst for selective detection of methylbenzenes. The selectivities of the 1.7 at % Pd-loaded $Co_3O_4$ yolk-shell spheres tended to decrease ($S_{xylene}/S_{ethanol}$=5.78 and $S_{toluene}/S_{ethanol}$=4.88) compared to those of the 0.17 at % Pd-loaded $Co_3O_4$ yolk-shell spheres. That is, the excess Pd decreased the catalytic effect of Pd on methylbenzenes. This is because the reactivity of the outer shells of the yolk-shell spheres was maximized, and as a result, methylbenzenes were completely decomposed or the excess Pd aggregated before penetration into the yolk-shell spheres.

FIG. 9 shows the responses of the gas sensors manufactured in Example 1 and Comparative Examples 1-1 and 1-2 to various gases at 275° C. (X: xylene, T: toluene, F: formaldehyde, B: benzene, E: ethanol, A: ammonia, and H: hydrogen). The gas sensors of Example 1, Comparative Example 1-1, and Comparative Example 1-2 showed the highest responses to xylene. The responses of the gas sensors of Comparative Example 1-1 and Comparative Example 1-2 to xylene gas were found to be 103 and 8.65, respectively, and the responses of the gas sensors of Comparative Example 1-1 and Comparative Example 1-2 to toluene gas were found to be 74.1 and 7.04, respectively. In contrast, the responses of the gas sensor of Example 1 to xylene and toluene gases were found to be 186 and 124, respectively, which were much higher than those of the gas sensors of Comparative Examples 1-1 and 1-2. These results indicate that the 0.86 at % Pd-loaded $Co_3O_4$ hollow hierarchical nanostructures (Example 1) were highly sensitive and selective to methylbenzenes.

FIG. 10 shows the responses of the gas sensors manufactured in Example 2 and Comparative Examples 2-1, 2-2, and 3 to various gases at 250° C. (X: xylene, T: toluene, F: formaldehyde, B: benzene, E: ethanol, A: ammonia, and H: hydrogen). The gas sensors of Example 2, Comparative Example 2-1, and Comparative Example 2-2 based on Pd-loaded $Co_3O_4$ yolk-shell spheres showed the highest responses to xylene gas while the gas sensor of Comparative Example 3 based on commercial $Co_3O_4$ powder showed very low responses to all gases. When Pd was loaded in an amount of 0.17 at %, the highest gas response was obtained ($S_{xylene}$=64.2). Rather, the loading of excess Pd (Comparative Example 2-2) decreased the gas responses ($S_{xylene}$=11.4). These results show that Pd should be loaded in an amount of at % for high sensitive and selective detection of methylbenzenes.

FIG. 11 shows the responses of the gas sensors manufactured in Examples 1 and 2 to xylene gas at varying concentrations (0.25-5.0 ppm). Both sensors showed different responses to xylene gas at different concentrations, demonstrating that the sensors can detect the concentrations of xylene and toluene in air in real time. Due to their high sensitivities, the sensors can detect gases at very low concentrations of 0.2 ppm.

Figure 12B:
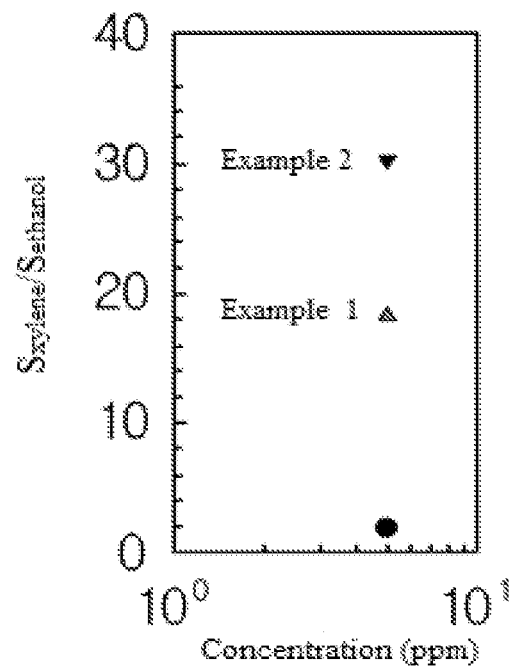
Figure 12C:
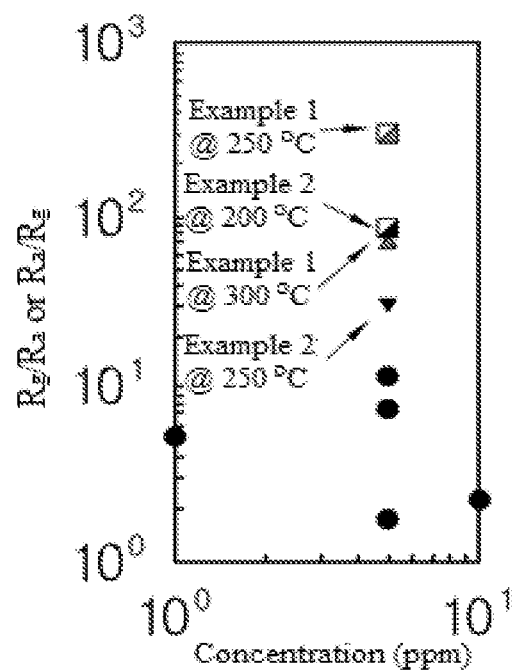
Figure 12D:
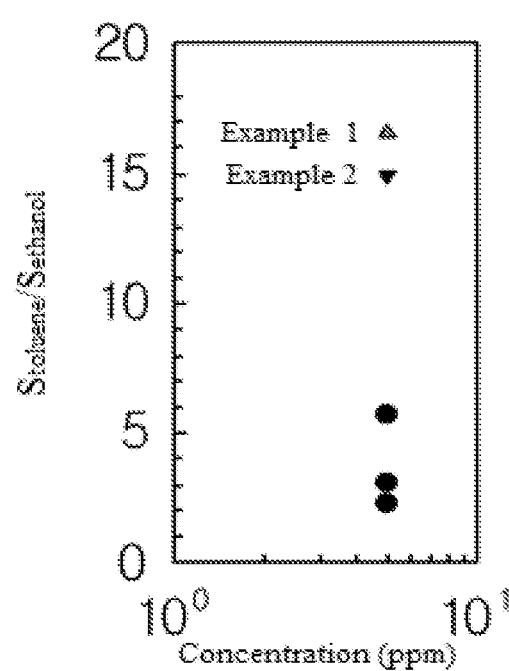

FIG. 12 compare the responses of the gas sensors manufactured in Examples 1 and 2 to methylbenzenes and the selectivities of the gas sensors to methylbenzenes over ethanol with those of conventional gas sensors reported in the literature. The results shown in (a) and (c) of FIG. 12 demonstrate that the gas sensors of Examples 1 and 2 have the highest responses to methylbenzenes (xylene and toluene) among oxide semiconductor gas sensors reported hitherto. (b) and (d) of FIG. 12 demonstrate that the selectivities of the gas sensors of Examples 1 and 2 to methylbenzenes are the highest ever achieved. These results can lead to the conclusion that oxide semiconductor gas sensors for detecting methylbenzenes with high sensitivity and high selectivity can be manufactured based on Pd-loaded $Co_3O_4$ hollow hierarchical nanostructures and yolk-shell spheres.

As is apparent from the forgoing, the oxide semiconductor gas sensor of the present invention is based on the use of Pd-loaded $Co_3O_4$ hollow hierarchical nanostructures or yolk-shell spheres. The response of the gas sensor according to the present invention to xylene gas at a concentration as low as 5 ppm is at least 150 times higher than that to ethanol gas. The gas sensor is based on the use of Pd-loaded $Co_3O_4$ hollow hierarchical nanostructures or yolk-shell spheres. The response of the gas sensor to toluene gas at a concentration as low as 5 ppm is at least 100 times higher than that to ethanol gas. In addition, the oxide semiconductor gas sensor of the present invention has the ability to selectively detect methylbenzene gases, including xylene and toluene (with at least 30-fold higher response to xylene and at least 15 times higher response to toluene than that to ethanol gas).

Conventional gas sensors show low responses to methylbenzene gases that are very large in molecular structure and are chemically stable. Conventional gas sensors cannot detect methylbenzene gases with high selectivity in the presence of formaldehyde and alcohol as highly reactive noise gases. In contrast, the gas sensor of the present invention can detect methylbenzene gases with high sensitivity and high selectivity and can selectively and accurately detect methylbenzene gases even at low concentrations.

Although the present invention has been described herein with reference to the preferred embodiments thereof, it is not limited to the embodiments and it will be understood by those skilled in the art that the invention can be implemented in other specific forms without departing from the spirit and scope of the invention as defined by the appended claims. The embodiments are merely illustrative and are not to be considered as limiting the invention in all aspects. The scope of the invention is defined by the appended claims rather than by the detailed description of the invention. All changes which come within the meaning and range of equivalency of the claims are to be encompassed within the scope of the invention.

EXPLANATION OF REFERENCE NUMERALS

120, 170 Gas sensing layers
110, 130 Electrodes

INDUSTRIAL APPLICABILITY

The gas sensor of the present invention can detect methylbenzene gases, such as xylene and toluene, which are harmful environmental gases that have similar influences on humans, with high sensitivity and high selectivity. In addition, the gas sensor of the present invention does not detect alcohol gas occurring during indoor activities, such as cooking and drinking, due to its low alcohol sensitivity and is thus advantageous in selectively sensing xylene and toluene. Furthermore, the gas sensor of the present invention is very advantageous in selectively sensing xylene and toluene because of its very low sensitivity to formaldehyde, which is usually detected at a high concentration indoors.

The gas sensor of the present invention uses palladium-loaded cobalt oxide nanostructures as raw materials that can be easily synthesized at one time on a large scale. According to the method of the present invention, the same sensing properties of the gas sensor can be obtained irrespective of how to add palladium and the structure of the cobalt oxide. Based on this, the methylbenzene gas sensor can bring better results in terms of selectivity over conventional gas sensors.

According to the present invention, the use of the palladium-loaded cobalt oxide nanostructures allows the p-type oxide semiconductor gas sensor to have greatly increased sensitivity and superior stability against external humidity.

The invention claimed is:

1. A gas sensor for detecting methylbenzene gases comprising a gas sensing layer comprising palladium (Pd)-loaded cobalt oxide ($Co_3O_4$) nanostructures having porous surface, wherein the palladium is loaded in an amount greater than 0 at % and no more than 1.7 at %, wherein the nanostructures are hollow hierarchical nanostructures in which plate-like primary particles aggregate to form spherical particles, or the nanostructures are yolk-shell spheres, and wherein the amount of the palladium is selected and the nano structures are configured such that the gas sensor has at least 15 times higher response to methylbenzene gases than to ethanol gas.

2. The gas sensor according to claim 1, wherein the nanostructures are hollow hierarchical nanostructures in which plate-like primary particles aggregate to form spherical particles.

3. The gas sensor according to claim 2, wherein the palladium is loaded in an amount of 0.86 at %.

4. The gas sensor according to claim 1, wherein the nanostructures are yolk-shell spheres.

5. The gas sensor according to claim 4, wherein the palladium is loaded in an amount of 0.17 at %.

6. The gas sensor of claim 1, wherein the amount of the palladium is selected and the nano structures are configured such that the gas sensor has at least 100 times higher response to toluene than to ethanol gas at a concentration of 5 ppm.

7. The gas sensor of claim 1, wherein the porous surface is formed from Pd-loaded cobalt oxide ($Co_3O_4$).

8. A method of detecting a methylbenzene gas comprising exposing a gas sensor of claim 1 to a target gas, and detecting the change in resistance when said gas sensor is exposed to air, wherein said gas sensor comprises a gas sensing layer comprising palladium (Pd)-loaded cobalt oxide ($Co_3O_4$) nanostructures.

9. The method of claim 8, wherein the nanostructures are hollow hierarchical nanostructures in which plate-like primary particles aggregate to form spherical particles.

10. The method of claim 9, wherein the palladium is loaded in an amount of 0.86 at %.

11. The method of claim 8, wherein the nanostructures are yolk-shell spheres.

12. The method of claim 11, wherein the palladium is loaded in an amount of 0.17 at %.

13. The method of claim 8, wherein the palladium is loaded in an amount greater than 0 at % and no more than 1.7 at %.

14. The method of claim 8, wherein the methylbenzene is xylene or toluene.

15. The method of claim 8, wherein concentration of the gas is about 5 ppm.

16. The method of claim 8, wherein the method is more selective to methylbenzene than to ethanol.

* * * * *